United States Patent
Newell et al.

(10) Patent No.: US 10,450,475 B2
(45) Date of Patent: Oct. 22, 2019

(54) TRAFFIC MARKING COMPOSITIONS CONTAINING POLYFUNCTIONAL AMINES

(71) Applicant: ENNIS PAINT, INC., Thomasville, NC (US)

(72) Inventors: Kevin Newell, Thomasville, NC (US); Haibo Li, High Point, NC (US); Jeremy Cheek, Winston Salem, NC (US)

(73) Assignee: Ennis Paint, Inc., Thomasville, NC (US)

(*) Notice: Subject to any disclaimer, the term of this patent is extended or adjusted under 35 U.S.C. 154(b) by 43 days.

(21) Appl. No.: 15/412,858

(22) Filed: Jan. 23, 2017

(65) Prior Publication Data

US 2017/0233598 A1    Aug. 17, 2017

Related U.S. Application Data

(63) Continuation-in-part of application No. 14/943,903, filed on Nov. 17, 2015.

(60) Provisional application No. 62/288,741, filed on Jan. 29, 2016.

(51) Int. Cl.
| | |
|---|---|
| C09D 5/14 | (2006.01) |
| C09D 133/00 | (2006.01) |
| C08F 220/14 | (2006.01) |
| C09D 5/02 | (2006.01) |
| C09D 133/12 | (2006.01) |
| C07C 225/12 | (2006.01) |
| C07D 295/088 | (2006.01) |
| C09D 7/63 | (2018.01) |
| C08K 5/3492 | (2006.01) |
| C08K 5/3462 | (2006.01) |
| C08K 5/17 | (2006.01) |
| C08K 5/103 | (2006.01) |
| C08K 5/00 | (2006.01) |

(52) U.S. Cl.
CPC .......... *C09D 133/00* (2013.01); *C07C 225/12* (2013.01); *C07D 295/088* (2013.01); *C08F 220/14* (2013.01); *C09D 5/024* (2013.01); *C09D 7/63* (2018.01); *C09D 133/12* (2013.01); *C08K 5/0025* (2013.01); *C08K 5/103* (2013.01); *C08K 5/17* (2013.01); *C08K 5/175* (2013.01); *C08K 5/3462* (2013.01); *C08K 5/3492* (2013.01); *C08K 5/34924* (2013.01); *C08K 5/34926* (2013.01)

(58) Field of Classification Search
CPC ................................ C09D 5/14; C09D 163/00
See application file for complete search history.

(56) References Cited

U.S. PATENT DOCUMENTS

| | | | |
|---|---|---|---|
| 3,673,022 A | 6/1972 | Iwami et al. | |
| 3,704,281 A | 11/1972 | Saran et al. | |
| 4,393,060 A * | 7/1983 | Fischer | C07D 405/14 |
| | | | 514/217.05 |
| 4,755,623 A | 7/1988 | Dileone | |
| 4,772,680 A | 9/1988 | Noomen et al. | |
| 5,349,026 A | 9/1994 | Emmons et al. | |
| 5,498,659 A | 3/1996 | Esser | |
| 5,527,853 A | 6/1996 | Landy et al. | |
| 5,539,073 A | 7/1996 | Taylor et al. | |
| 5,939,195 A * | 8/1999 | Allen | B05D 7/534 |
| | | | 428/413 |
| 5,939,514 A | 8/1999 | Brown et al. | |
| 6,028,141 A | 2/2000 | Singh et al. | |
| 6,075,079 A | 6/2000 | Helmer et al. | |
| 6,262,169 B1 | 7/2001 | Helmer et al. | |
| 7,985,424 B2 | 7/2011 | Tomalia et al. | |
| 10,246,571 B2 | 4/2019 | Li | |
| 2007/0100074 A1* | 5/2007 | Devonport | C09D 133/02 |
| | | | 525/107 |
| 2015/0259562 A1 | 9/2015 | Li et al. | |

FOREIGN PATENT DOCUMENTS

| | | |
|---|---|---|
| WO | 2014/060456 A3 | 4/2014 |
| WO | 2014/111292 A1 | 7/2014 |

OTHER PUBLICATIONS

ASTM D7377-09(2013), Standard Practice for Evaluating the Water Wash-Off Resistance of Traffic Paints using a Water Faucet, ASTM International, West Conshohocken, PA, 2013, www.astm.org.
ASTM D562-10(2014), Standard Test Method for Consistency of Paints Measuring Krebs Unit (KU) Viscosity Using a Stormer-Type Viscometer, ASTM International, West Conshohocken, PA, 2014, www.astm.org.
ASTM D711-10(2015), Standard Test Method for No-Pick-Up Time of Traffic Paint, ASTM International, West Conshohocken, PA, 2015, www.astm.org.
ASTM D870-09, Standard Practice for Testing Water Resistance of Coating Using Water Immersion, ASTM International, West Conshohocken, PA, 2015, www.astm.org.
(Continued)

*Primary Examiner* — Gregory Listvoyb
(74) *Attorney, Agent, or Firm* — Kilpatrick Townsend & Stockton LLP

(57) ABSTRACT

Disclosed are aqueous coating compositions containing an anionically stabilized polymer, one or more polyfunctional amines acting as crosslinking agents, and a volatile base. Coating compositions can further include one or more additional copolymers, which may or may not be anionically stabilized, and/or additional additives, including pigments, defoamers, pigment dispersing agents, thickeners, surfactants, and combinations thereof. By incorporating one or more polyfunctional amines, such as those comprising recurring units derived from the reaction of one tri-glycidyl moiety and a single di-, or tri-functional amino monomer, or a combination of mono/bi, mono/tri, mono/tetra, bi/bi, bi/tri, bi/tetra, tri/tri, tri/tetra, and tetra/tetra functional amino monomers with a bi- or tri-glycidyl moiety, water wash-off resistance of the coating compositions which comprise paint formulations, can be increased.

19 Claims, No Drawings

(56) References Cited

OTHER PUBLICATIONS

ASTM D2486-00, Standard Test Methods for Scrub Resistance of Wall Paints, ASTM International, West Conshohocken, PA, 2000, www.astm.org.
ASTM D2805-96a, Standard Test Methods for Hiding Power of Paints by Reflectrometry, ASTM International, West Conshohocke PA, 1996, www.astm.org.
PCT/US2017/014546, "International Search Report and Written Opinion", dated Apr. 26, 2017, 11 pages.

* cited by examiner

TRAFFIC MARKING COMPOSITIONS CONTAINING POLYFUNCTIONAL AMINES

CROSS-REFERENCES TO RELATED APPLICATIONS

This application is a nonprovisional of and claims priority under 35 USC 120 to provisional application 62/288,741 filed Jan. 29, 2016 and entitled "Traffic Marking Compositions Containing Polyfunctional Amines".

This is a continuation-in-part of and claims priority to U.S. Nonprovisional application Ser. No. 14/943,903 entitled "Polyfunctional Amines with Hydrophobic Modification for Controlled Crosslinking of Latex Polymers" filed on Nov. 17, 2015.

FIELD OF THE INVENTION

Disclosed herein are aqueous coating compositions containing an anionically stabilized polymer, one or more polyfunctional amines, and a volatile base. Coating compositions can further include one or more additional copolymers, which may or may not be anionically stabilized, and/or additional additives, including pigments, defoamers, pigment dispersing agents, thickeners, surfactants, and combinations thereof. By incorporating a polyfunctional amine, such as those comprising recurring units derived from the reaction of one tri-glycidyl moiety and a single di-, or tri-functional amino monomers, or combination of mono/bi, mono/tri, mono/tetra, bi/bi, bi/tri, bi/tetra, tri/tri, tri/tetra, and tetra/tetra functional amino monomers with a bi- or tri-glycidyl moiety, the setting time (and drying time) of the coating compositions can be decreased. Also provided are coatings formed from the coating compositions described herein, as well as methods of forming these coatings.

The present disclosure relates generally to fast-drying coating compositions containing polyfunctional amines for use in a variety of applications.

BACKGROUND OF THE INVENTION

The formation of durable, high quality coatings on exterior surfaces, more particularly roadway surfaces, poses numerous challenges. Notably, coatings on exterior surfaces typically remain exposed to the elements during application and drying. As a result, weather conditions during coating application and drying can impact the quality of exterior coatings. In particular, rainfall during and/or after coating applications can wash off some or all of the coating, resulting in coating failure.

By shortening the setting time of coatings, instances of coating failure, such as those due to unanticipated rainfall, can be minimized. Towards this end, additives have been incorporated into coatings to decrease setting time and increase water wash-off resistance. While coatings containing setting additives do exhibit fast drying behavior, these coatings suffer from serious physical property drawbacks, including decreased elongation at break and significant yellowing upon weathering. As a result, existing fast drying coatings have proved unsuitable for many applications. The invention described herein addresses this long felt need.

SUMMARY OF THE DISCLOSURE

Disclosed are fast drying aqueous coating compositions comprising; an anionically stabilized copolymer, a polyfunctional amine, and a volatile base exhibiting improved early water (water wash-off) resistance. These coatings exhibit fast drying times upon application to a surface. In addition, the coating compositions display suitable physical properties for a wide variety of exterior coating/paint applications.

The coating compositions contain one or more anionically stabilized polymers. The coating compositions also contain a polyfunctional amine, such as those comprising recurring units derived from the reaction of one tri-glycidyl moiety and a single di-, or tri-functional amino monomers, or combination of mono/bi, mono/tri, mono/tetra, bi/bi, bi/tri, bi/tetra, tri/tri, tri/tetra, and tetra/tetra functional amino monomers with a bi- or tri-glycidyl moiety, or a combination thereof.

Suitable polyfunctional amines can possess a variety of molecular weights and degrees of nitrogen-derivatization. For example, the polyfunctional amine can have an average molecular weight of between 100 and 500,000 Daltons and/or a degree of nitrogen-derivatization between 5% and 100%. In some embodiments, the polyfunctional amine is present in the coating composition at between 0.1% by weight and 2.5% by solid weight of the polyfunctional amine to the total weight of the coating/paint formulae.

The coating compositions also contain a volatile base. Exemplary volatile bases include, but are not limited to, ammonia, lower alkylamines such as dimethylamine and diethylamine, ethanolamine, morpholine, aminopropanol, 2-amino-2-methyl-1-propanol, 2-dimethylaminoethanol, and combinations thereof. In certain embodiments, the volatile base is ammonia.

Coating compositions can further contain an additional polymer. The additional polymer can be, for example, a polymer or copolymer derived from one or more (meth) acrylate monomers, vinyl aromatic monomers, ethylenically unsaturated aliphatic monomers, vinyl ester monomers, and combinations thereof. The coating compositions can also include one or more additives, including pigments, fillers, dispersants, coalescents, pH neutralizing agents, plasticizers, defoamers, surfactants, thickeners, biocides, co-solvents, and combinations thereof.

Also provided are coatings formed from the coating compositions described herein, as well as methods of forming these coatings and/or paints. Generally, coatings are formed by applying a coating composition described herein to a surface, and allowing the coating to dry to form a coating. The resultant dry coatings typically comprise, at minimum, an anionically stabilized polymer and a polyfunctional amine. The dry coatings can further comprise one or more additional polymers and/or additives as described above. The coating thickness can vary depending upon the application of the coating. In some embodiments, the coating has a dry thickness of between 5 mils and 20 mils. In general, the coating must have a change in viscosity, provided as a change in Krebs Units (AKU) of 10 KU or less after being placed in an oven for 14 days, according to the ASTM D-562 standard.

The coating compositions can be applied to a variety of surfaces including, but not limited to metal, asphalt, concrete, stone, ceramic, wood, plastic, polymer, polyurethane foam, glass, and combinations thereof. The preferred surfaces of this disclosure are those used in roadway paving and surfacing. The coating compositions can be applied to interior or exterior surfaces.

The details of one or more embodiments are set forth in the description below. Other features, objects, and advantages will be apparent from the description and from the claims.

DETAILED DESCRIPTION OF THE INVENTION

As used herein, the term "(meth)acrylate monomer" includes acrylate, methacrylate, diacrylate, and dimethacrylate monomers.

The coating compositions described herein contain one or more anionically stabilized polymers. In some embodiments, the anionically stabilized polymer includes an acrylic-based copolymer. In certain instances, the acrylic-based copolymer is derived from two or more, three or more, or four or more (meth)acrylate monomers. In particular embodiments, the acrylic-based copolymer is derived from one or more (meth)acrylate monomers selected from the group consisting of methyl methacrylate, butyl acrylate, 2-ethylhexylacrylate, and combinations thereof.

The emulsion polymerization can be carried out as a batch process, as a semi-batch process, or in the form of a continuous process. In some embodiments, a portion of the monomers can be heated to the polymerization temperature and partially polymerized, and the remainder of the monomer batch can be subsequently fed to the polymerization zone continuously, in steps, or with superposition of a concentration gradient. In some embodiments, the copolymer is produced in a single stage (i.e., does not include separate feeds having different monomer compositions so as to produce a multistage polymer particle such as a core/shell particle).

The emulsion polymerization can be performed with a variety of auxiliaries, including water-soluble initiators and regulators. Reduction-oxidation (redox) initiator systems are also suitable as initiators for the emulsion polymerization.

Dispersants, such as surfactants, can also be added during polymerization to help maintain the dispersion of the monomers in the aqueous medium. Anionic and nonionic surfactants can be used during polymerization. The coating compositions described herein further contain one or more polyfunctional amines. The polyfunctional amine functions as a fast drying agent and decreases the setting time of the coating compositions.

Polyfunctional amines are compounds which contain a plurality of primary amine groups, secondary amine groups, or combinations thereof. Generally, the polyfunctional amine contains at least three primary amine groups, secondary amine groups, or combinations thereof. The polyfunctional amine can be a polymer or copolymer derived from one or more monomers containing an amine group. In some embodiments, the polyfunctional amine is an acrylic polymer derived from one or more monomers comprising an amino group.

Polyfunctional amines, as described herein are polyamines that are N-derivatized such that one or more amine nitrogens have been derivatized (i.e., some number of the primary and/or secondary amine groups within the polyamine have been covalently modified to replace one or more hydrogen atoms in the primary and/or secondary amine groups with a non-hydrogen moiety). For example, in the case of polyamines containing one or more primary amine groups, polyfunctional amines can include polyamines where at least a portion of the primary amine groups have been converted to either secondary or tertiary amine groups. In the case of polyamines containing one or more secondary amine groups, polyfunctional amines can include polyamines where at least a portion of the secondary amine groups have been converted to tertiary amines.

Suitable polyfunctional amines are known in the art, and include polyamines in which some number of the primary and/or secondary amine groups have been covalently modified to replace one or more hydrogen atoms with a non-hydrogen moiety (R). The R groups present within a polyfunctional amine can be selected such that the polyfunctional amine possesses a hydrophilicity which renders the polyfunctional amine compatible with the aqueous compositions described herein. For example, the R groups within the polyfunctional amine can be selected such that the polyfunctional amine is water soluble or water dispersible.

Polyfunctional amines are generally incorporated into the compositions in amounts less than 10% by weight, based on the dry weight of the anionically stabilized copolymer. The amount of polyfunctional amine present in the composition can be selected in view of the identity of the polyfunctional amine, the nature of the anionically stabilized copolymer present in the composition, and the desired setting time of the composition.

In some embodiments, the polyfunctional amine is present in the composition at between 0.1% by weight and 5% by weight, based on the dry weight of the anionically stabilized copolymer. In certain embodiments, the polyfunctional amine is present in the composition at between 0.5% by weight and 2.5% by weight, based on the dry weight of the anionically stabilized copolymer.

Polyfunctional amines having a range of molecular weights and degrees of nitrogen-derivatization can be incorporated into the coating compositions. The setting time of the composition, as well as the physical properties of the resultant coating, can be varied by selection of the loading level, molecular weight, microstructure (e.g., degree of branching), and the degree of nitrogen-derivatization of the polyfunctional amine. The setting time of the composition, as well as the physical properties of the resultant coating, can also be influenced by ambient conditions during coating application and drying, including humidity and temperature. In some embodiments, a particular polyfunctional amine is incorporated into the coating composition at a particular loading level in view of ambient conditions, including humidity and temperature, to achieve a coating having a desired setting time, desired physical properties, or a combination thereof.

In some embodiments, the polyfunctional amines have a weight average molecular weight of varying from about 100 to 500,000 Daltons; more preferably from 500 to 100,000 and most preferably from 1,000 to 20,000. Since the polymers of the present invention become highly crosslinked upon drying, there is no substantial disadvantage to starting with very low molecular weight polymers.

The fast drying coating compositions described herein also contain a volatile base. Volatile bases are basic substances that are soluble in water, remain in the aqueous coating composition under normal storage conditions, and evaporate from the aqueous coating composition under suitable drying conditions.

Generally, one or more volatile bases are incorporated in the composition in an effective amount to maintain the pH of the coating composition in the range of from 7.5 to 12.5 or in the range from 9 to 11. In some embodiments, one or more volatile bases are incorporated in the composition at between 0.1% by weight and 5.0% by weight. In certain embodiments, one or more volatile bases are incorporated in the composition at between 0.5% by weight and 2.5% by weight.

Suitable volatile bases can be selected on the basis of several factors, including their basicity and volatility. Exemplary volatile bases include, but are not limited to, ammonia, lower alkylamines such as dimethylamine, triethylamine, and diethylamine, ethanolamine, diethanolamine, triethanolamine, morpholine, aminopropanol, 2-amino-2-methyl-1-propanol, 2-dimethylaminoethanol, and combinations thereof. In certain embodiments, the volatile base is ammonia. In some cases, ammonia is the sole volatile base present in the coating composition. Alternatively, ammonia can be incorporated in admixture with other volatile bases, non-volatile bases, such as alkali metal hydroxides, or combinations thereof.

The aqueous coating compositions can further include one or more additives, including pigments, fillers, dispersants, coalescents, pH modifying agents, plasticizers, defoamers, surfactants, thickeners, biocides, co-solvents, and combinations thereof. The choice of additives in the composition will be influenced by a number of factors, including the nature of the acrylic polymer dispersion and the intended use of the coating composition.

Other suitable additives that can optionally be incorporated into the composition include rheology modifiers, wetting and spreading agents, leveling agents, conductivity additives, adhesion promoters, anti-blocking agents, anti-cratering agents and anti-crawling agents, anti-freezing agents, corrosion inhibitors, anti-static agents, flame retardants and intumescent additives, dyes, optical brighteners and fluorescent additives, UV absorbers and light stabilizers, chelating agents, cleanability additives, crosslinking agents, flatting agents, flocculants, humectants, insecticides, lubricants, odorants, oils, waxes and slip aids, soil repellants, stain resisting agents, and combinations thereof.

The coating compositions described above can be provided as aqueous dispersions having a volume solids content of from 45-65% or from 60-77% by weight of the total paint formulation.

Also provided are coatings formed from the coating compositions described herein, as well as methods of forming these coatings. Generally, coatings are formed by applying a coating composition described herein to a surface, and allowing the coating to dry to form a coating. The resultant dry coatings typically comprise, at minimum, an anionically stabilized polymer and a polyfunctional amine. The dry coatings can further comprise one or more additives (e.g., pigments and/or fillers) as described above.

Coating compositions can be applied to a surface by any suitable coating technique, including spraying, rolling, brushing, or spreading. Coating compositions can be applied in a single coat, or in multiple sequential coats (e.g., in two coats or in three coats) as required for a particular application. Generally, the coating composition is allowed to dry under ambient conditions. However, in certain embodiments, the coating composition can be dried, for example, by heating and/or by circulating air over the coating.

Coating thickness can vary depending upon the application of the coating.

The coating compositions can be applied to a variety of surfaces including, but not limited to metal, asphalt, concrete, stone, ceramic, wood, plastic, polyurethane foam, glass, and combinations thereof. The coating compositions can be applied to interior or exterior surfaces.

In certain embodiments, the coating is applied to a surface to reflect solar radiation. In these cases, the coating will generally contain one or more pigments that reflect solar energy, such as titanium dioxide. By reflecting the sun's heat, the coating can help to cool a surface. In the case of coatings applied to architectural surfaces such as roofs, the roof coating can help to reduce a building's interior temperatures and cooling costs.

In some embodiments, the coating is applied to a road surface as traffic paint. In these embodiments, the road surface can be, for example, asphalt or concrete. In some cases when the coating is applied as traffic paint, the coating contains a filler such as a reflective filler.

Polyfunctional amines can also be incorporated as fast drying agents in other types of compositions which contain anionically stabilized copolymers. In particular, polyfunctional amines may be utilized to decrease the setting time of other compositions where fast setting and/or rain resistance are desirable.

SUMMARY

In summary, the present disclosure provides for an aqueous coating composition (that may be an aqueous latex paint) comprising:

(a) one or more anionically stabilized acrylic copolymer;

(b) one or more polyfunctional amines of a structure as provided by I-x[-b]-1 and/or I-x[-b]-2';

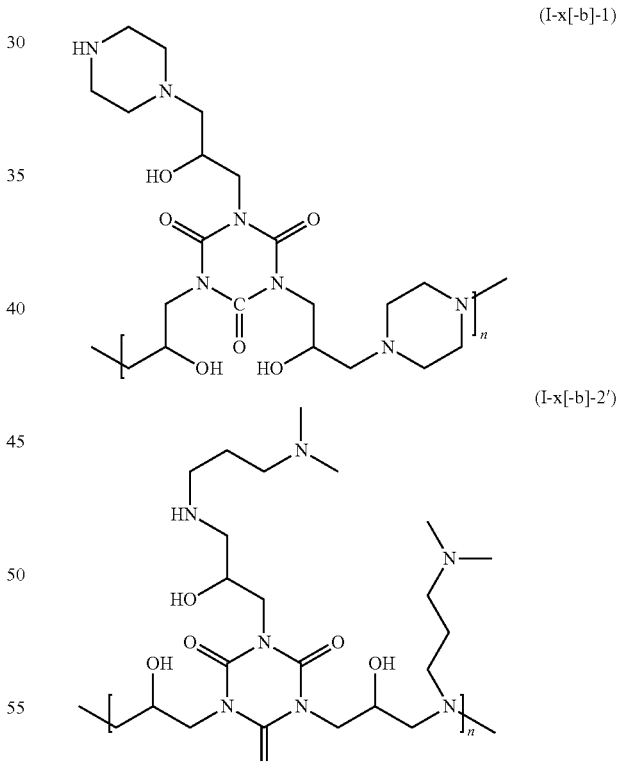

and;

(c) at least one volatile base.

More specifically, the polyfunctional amines may further include one or more variations of structures I-x[-b]-1 and I-x[-b]-2' provided as I-x[-b]-1' and I-x[-b]-2" so that a final polyfunctional amine structure is partially or fully saturated and/or highly branched wherein:

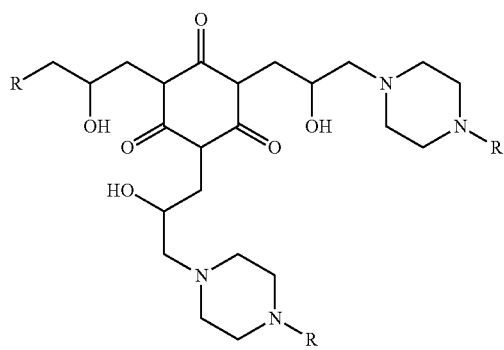

and where R=H or a next repeating unit,
and where the next repeating unit is represented as (I-x[-b]-1'-RU)

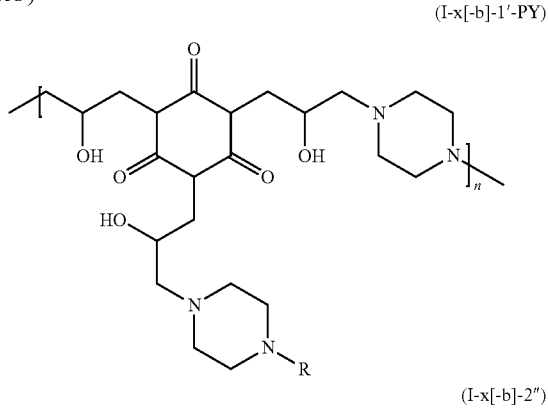

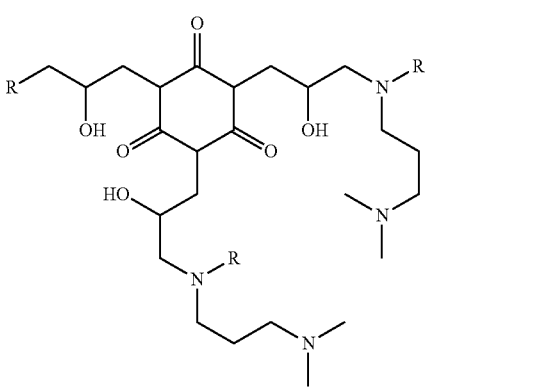

and where R=H or the next repeating unit
and where the next repeating unit is represented as (I-x[-b]-2"-RU)

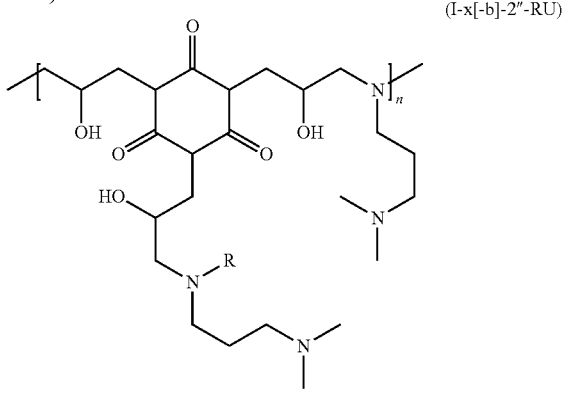

and where n is a number between 1 and 100,
and where $M_n$ is 5,000 to 20,000 Daltons.

In a further embodiment, the aqueous latex paint provides for dry times on paved surfaces in an atmosphere that is characterized as possessing at least 50% and up to 75% relative humidity with a final ΔKu value of no greater than 10.0, as measured using ASTM D711.

Additionally, the aqueous latex paint provides for water resistance that reduces or eliminates blistering, wherein the aqueous latex paint is tested according to ASTM D870 for water immersion.

Also, the latex paint provides for water resistance that improves scrub resistance as compared to said aqueous latex paint with commercially available quick drying agents (CQDA's) by at least 30% wherein the paint is tested according to ASTM D 2486 for water immersion.

Further, the latex paint provides for water resistance that improves color fastness by improving opacity to at least 98% as compared to aqueous latex paint with commercially available quick drying agents (CQDA's) wherein the paint is tested according to ASTM D 2850 for color opacity.

The aqueous latex paint may contain only white pigment or yellow pigment.

The aqueous latex paint contains polyfunctional amines having average molecular weights of between 100 and 500,000 Daltons and more preferably an average molecular weight of between 5,000 and 20,000 Daltons.

The aqueous latex composition may be present in the paint at between 0.1% by weight and 5% by weight, based on a dry weight of an anionically stabilized copolymer.

The aqueous latex paint may be present at between 0.5% by weight and 2.5% by weight, based on a dry weight of the anionically stabilized copolymer.

The aqueous latex paint may be comprised of one or more additional polymers and the paint may include additional pigments, fillers, dispersants, coalescents, pH modifying agents, plasticizers, defoamers, surfactants, thickeners, biocides, co-solvents, and combinations thereof.

Additional additives integrated into the paint may include rheology modifiers, wetting and spreading agents, leveling agents, conductivity additives, adhesion promoters, anti-blocking agents, anti-cratering agents and anti-crawling agents, anti-freezing agents, corrosion inhibitors, anti-static agents, flame retardants and intumescent additives, dyes, optical brighteners and fluorescent additives, UV absorbers and light stabilizers, chelating agents, cleanability additives, crosslinking agents, flatting agents, flocculants, humectants, insecticides, lubricants, odorants, oils, waxes and slip aids, soil repellants, stain resisting agents, and combinations thereof.

The aqueous latex paint may include aqueous dispersions having a volume solids content of between 45 and 65% by weight of a total paint formulation.

The aqueous latex paint may more preferably include aqueous dispersions having a volume solids content of between 60 and 77% by weight of a total paint formulation.

The coating compositions may be applied to a surface selected from the group consisting of metal, asphalt, concrete, stone, ceramic, wood, plastic, polyurethane foam, glass, and combinations thereof.

The coating compositions may have a dry coating (often a film) thickness of between 10 mils and 100 mils.

One method for making an aqueous latex paint comprising one or more polyfunctional amines with structures (I-x[-b]-1) and/or (I-x[-b]-2') added as crosslinkers is described by;

(i) obtaining a first vessel filled with an aqueous polymer acrylic based emulsion and adding at least 1% of at least one of polyfunctional amine crosslinkers followed by stirring for 5 minutes using a high sheer mixing blade at moderate speeds;

(ii) adding to a second vessel, a mixture of a defoamer, a nonionic surfactant, a dispersant polymer combination, a biocide, and a thickener that is pre-mixed with water wherein (iii) the mixture is added to the first vessel while stirring with a high sheer mixing blade at a moderate speed for at least 5 minutes and;

(iv) adding to the first vessel a rheology modifier and water and stirring an overall mixture at high speed for at least another 5 minutes and (v) subsequently adding ammonia in an amount required to obtain an overall solution of pH 10 followed by pigments and fillers including titanium dioxide, calcium carbonate, and silica added while stirring at high speed for at least 15 minutes and (vi) after completing mixing and accompanying grinding, a solvent is added slowly and at reduced stirring speeds with propylene glycol and a waterborne float solution intermediate wherein the latex paint is completed when a coalescent is added to a final mixture during continuous stirring.

By way of non-limiting illustration, examples of certain embodiments of the present disclosure are given below.

EXAMPLES

Examples of compositions containing polyfunctional amine crosslinkers as fast drying agents in latex compositions are provided herein. As these formulations are preferably used as traffic markings or roadway markings with the colors white and yellow provided. The selection of these specific colored embodiments in no way are suggested as a limitation of the disclosure.

Acrylic Latex Compositions Containing a Polyfunctional Amine Crosslinker as a Fast Drying Agent (White)

Acrylic latex compositions containing a polyfunctional amine crosslinker as a fast-drying additive for white marking compositions are given as provided in Table 1.

Elastomeric coatings (white and yellow are the preferred colors obtained primarily by using inorganic pigments, but other colors are possible as well) containing at least one anionically stabilized acrylic-based copolymer and at least one polyfunctional amine with the structures (I-x[-b]-1) and (I-x[-b]-2') and modifications thereof (as shown below) are described. The use of a commercially available quick drying agent (CQDA) such as a polyfunctional amine that is a known alkoxylated polyalkyleneimine was also prepared as a basis for comparison.

Examples 1-4 provide details of these coating formulations for producing white pigmented compositions. Examples 5-8 provide details of these coating formulations for producing yellow pigmented compositions.

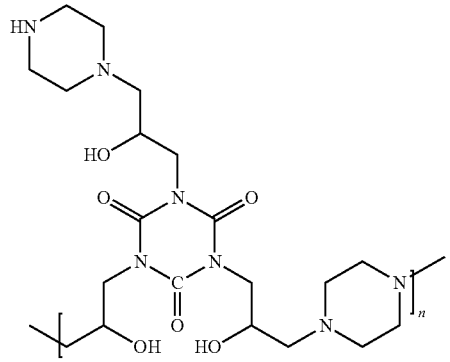

(I-x[-b]-1)

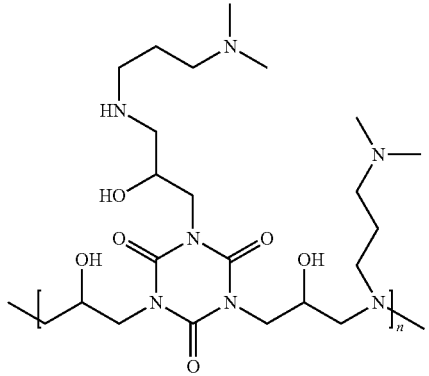

(I-x[-b]-2')

Additional embodiments regarding the I-x[-b]-1 and I-x[-b]-2' structures include variations, provided as I-x[-b]-1' and I-x[-b]-2" below indicating that the final polyfunctional amine can be partially or fully saturated and/or highly branched:

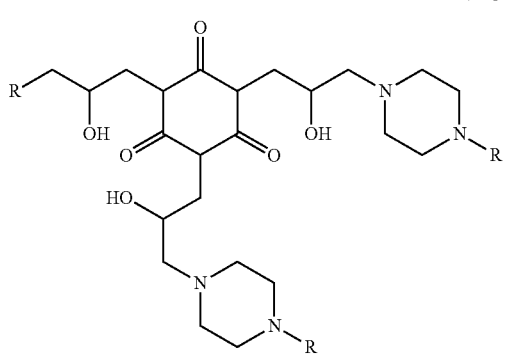

(I-x[-b]-1')

where R═H or the next repeating unit
and where the next repeating unit is represented as (I-x[-b]-1'-RU)

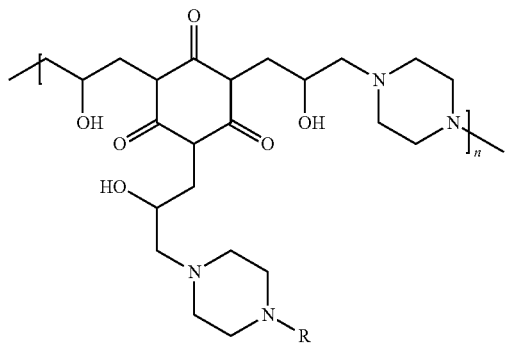

(I-x[-b]-1'-RU)

and wherein n is equal to a number 1 to 100
and where $M_n$ is 5,000 to 20,000 Daltons.

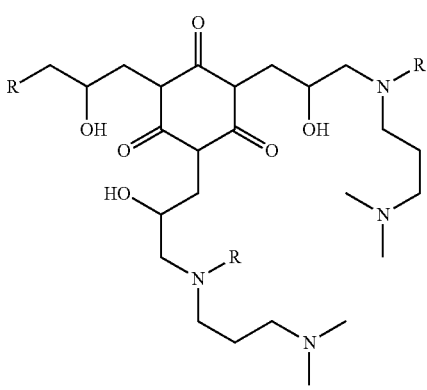

(I-x[-b]-2″)

where R=H or the next repeating unit
and where the next repeating unit is represented as (I-x[-b]-2″-RU)

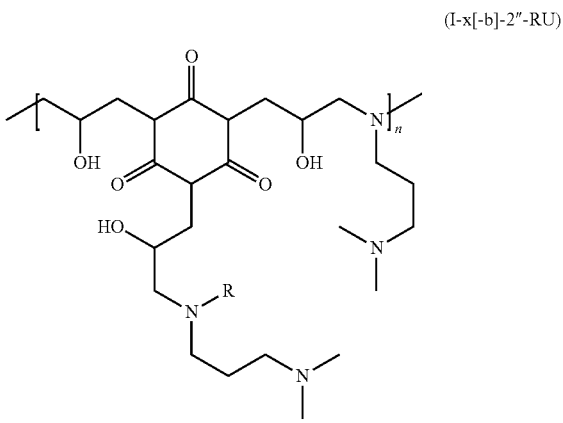

(I-x[-b]-2″-RU)

and where n is equal to a number 1 to 100
and where $M_n$ is 5,000 to 20,000 Daltons.

To ensure that the polyfunctional amines shown above and listed as (I-x[-b]-1), (I-x[-b]-2'), (I-x[-b]-1'), (I-x[-b]-1'-RU) and (I-x[-b]-2″-RU) are properly synthesized, the stoichiometric reaction ratios between amine monomers and glycidyl monomers must be carefully controlled. These optimal ratios are obtained by using the following general equation;

$$(2+1/m):1 - \text{the ratio of amine groups}(2+1/m) \text{ to epoxy groups}(:1) \quad (1)$$

Where m=1-100 and is the number of repeating amine units

Example 1

For a 100 gallon coating composition, the following ingredients were mixed together
to produce a white paint composition containing a polyfunctional amine according to the structure (I-x[-b]-2'), to a vessel containing 458.0 lb of in-house aqueous polymer emulsion, also referred to as EF Acrylic Latex 1, was added 11 lb of the polyfunctional amine crosslinker solution (I-x[-b]-2') and stirred for 5 minutes using a high sheer mixing blade at a moderate speed. While mixing this solution, 7.0 lb defoamer, 5.0 lb octylphenol ethoxylate nonionic surfactant, 8 lb of a high performance dispersant polymer combination, 0.2 lb biocide, and 0.3 lb thickener was pre-mixed with 11.3 lb of water and subsequently added to the Latex 1 emulsion with crosslinker and allowed to continue stirring with a high sheer mixing blade at a moderate speed for another 5 minutes. Next, 0.3 lb rheology modifier was mixed with 10.6 lb of water and added to the stirring mixture and stirred at high speed for another 5 minutes. To this, approximately 18.9 lb ammonia (not less) was added to obtain a solution of pH 10. Then pigments and fillers including 140 lb Titanium dioxide, 510.0 lb Calcium carbonate, and 150 lb silica were added carefully while stirring at high speed for an additional 15 minutes. After completion of the mixing and accompanying grinding, 35 lb of a solvent (methyl alcohol in this case although other alcohols and ketones could be substituted) was added slowly while reducing the stirring speed together with the addition of 3.0 lb propylene glycol and 10 lb of a waterborne float solution intermediate. Finally, 20.0 lb of a coalescent solvent such as 2,2,4-Trimethyl-1,3-pentanediol monoisobutyrate was added to the mixture, while stirring continued.

Example 2

For a 100 gallon coating composition, the following ingredients were mixed to achieve a white paint composition:
a white paint composition containing a polyfunctional amine of the (I-x[-b]-1) structure shown was provided by adding 458.0 lb of in-house aqueous polymer emulsion, also referred to as EF Acrylic Latex 1 to a vessel to which was added 11 lb of the polyfunctional amine crosslinker (1-x[-b]-1) and stirred for 5 minutes using a high sheer mixing blade at moderate speed. In an identical manner as described in Example 1 above, while mixing this solution, 7.0 lb defoamer, 5.0 lb octylphenol ethoxylate nonionic surfactant, 8 lb of a high performance dispersant polymer combination, 0.2 lb biocide, and 0.3 lb thickener was pre-mixed with 11.3 lb of water and subsequently added to the Latex 1 emulsion with the (I-x[-b]-1) crosslinker and allowed to continue stirring with a high sheer mixing blade at a moderate speed for another 5 minutes. To this, approximately 10 lb ammonia, or more was added to obtain a solution of pH 10. Then pigments and fillers including 140 lb titanium dioxide, 510 lb calcium carbonate, and 150 lb silica were added carefully while stirring at high speed for 15 minutes. After completion of the mixing and accompanying grinding, 35 lb of the solvent as described in Example 1 was added slowly and at reduced stirring speed together with 3.0 lb propylene glycol and 10 lb of a waterborne float solution intermediate. Then 10 g glycol ether solvent and 10 lb of a coalescent solvent such as 2,2,4-Trimethyl-1,3-pentanediol monoisobutyrate, were added to the mixture and this mixture was allowed to continuously stir.

Example 3

For a third 100 gallon white paint (coating composition), the following ingredients were mixed as follows;

a white paint composition containing a polyfunctional amine of the (I-x[-b]-2') structure shown was provided by adding 458.0 lb of in-house aqueous polymer emulsion, also referred to as EF Acrylic Latex 1 to a vessel to which was added 11 lb of the polyfunctional amine crosslinker (1-x[-b]-2') and stirred for 5 minutes using a high sheer mixing blade at moderate speed. While mixing this solution, 7.0 lb defoamer was added, 6 lb Polycarboxylic acid dispersant, 5 lb grind aid surfactant, 4 lb amine alkoxylate stabilizing surfactant dispersion, 0.2 lb biocide, and 0.3 lb thickener were pre-mixed with 11.3 lb of water and added to the emulsion containing the (1-x[-b]-2') polyfunctional amine crosslinker while stirring with a high sheer mixing blade at a moderate speed for another 5 minutes. Next, 0.3 lb of a rheology modifier was mixed with 9.8 lb of water and added to the stirring mixture and stirred at high speed for another 5 minutes. To this solution, approximately 2 lb ammonia (an amount added to ensure reaching a pH of 10) or more was added to obtain a solution of pH 10. Next pigment and fillers comprising 140 lb Titanium dioxide 510 lb Calcium carbonate and 150 lb silica were added carefully while stirring at high speed for 15 minutes. After completion of the mixing and accompanying grinding, 35 lb of a solvent (as described in Example 1) was added slowly and at a reduced stirring speed together with 3.0 lb propylene glycol and 10 lb of a waterborne float solution intermediate (93¬98% water, 0-6% Propylene Glycol, and 1-2% ammonium hydroxide by wt). Then 20.0 lb of the coalescent was added to the mixture and stirring was allowed to continue.

Example 4

For a fourth 100 gallon white paint (coating composition), the following ingredients were mixed as follows;

a white paint composition containing a commercially available quick drying agent (CQDA) was provided by adding 458.0 lb of in-house aqueous polymer emulsion, also referred to as EF Acrylic Latex 1 to a vessel to which was added 11 lb of the commercially available quick drying agent (CQDA) and stirred for 5 minutes using a high sheer mixing blade at moderate speed. While mixing this solution, 7.0 lb defoamer was added, 6 lb Polycarboxylic acid dispersant, 5 lb grind aid surfactant, 4 lb amine alkoxylate stabilizing surfactant dispersion, 0.2 lb biocide, and 0.3 lb thickener were pre-mixed with 11.3 lb of water and added to the emulsion containing the (1-x-[b-]2') polyfunctional amine crosslinker while stirring with a high sheer mixing blade at a moderate speed for another 5 minutes.

Next, 0.3 lb rheology modifier was added to the stirring mixture and stirred at high speed for another 5 minutes. To this solution, approximately 2 lb ammonia (an amount added to ensure reaching a pH of 10) or more was added to obtain a solution of pH 10. Next pigment and fillers comprising 140 lb Titanium dioxide 510 lb Calcium carbonate and 150 lb silica were added carefully while stirring at high speed for 15 minutes. After completion of the mixing and accompanying grinding, 35 lb of a solvent (as described in Example 1) was added slowly and at a reduced stirring speed together with 3.0 lb propylene glycol and 10 lb of a waterborne float (93-98% water, 0-6% Propylene Glycol, and 1-2% ammonium hydroxide by wt) solution intermediate. Then 20.0 lb of the coalescent was added to the mixture and stirring was allowed to continue.

Table 1 provided below summarizes the four different white paint (coating) compositions described above.

TABLE 1

Acrylic Latex Compositions Containing a Polyfunctional Amine Crosslinker as a Fast Drying Agent (White)—All numbers correspond to weight in pounds of each additive

| Description | Example 1 | Example 2 | Example 3 | Example 4 |
|---|---|---|---|---|
| Acrylic Latex Dispersant | | 8.0 | | |
| Polycarboxylic Acid Dispersant | | | 6.0 | 6.0 |
| Octylphenol ethoxylate nonionic surfactant | 5.0 | 5.0 | | |
| Biocide | 0.2 | 0.2 | 0.2 | 0.2 |
| Thickener | 0.3 | 0.3 | 0.3 | 0.3 |
| Rheology Modifier | 0.3 | 0.3 | 0.3 | 0.3 |
| Defoamer | 7.0 | 7.0 | 7.0 | 7.0 |
| Grind Aid Surfactant | | | 5.0 | 5.0 |
| Amine alkoxylate Stabilizing Surfactant Dispersant | | | 4.0 | 4.0 |
| High-Performance Dispersant Polymer Combination | 8.0 | | | |
| CQDA | 0.0 | 0.0 | 0.0 | 11.0 |
| Calcium Carbonate | 510.0 | 510.0 | 510.0 | 510.0 |
| Silica | 150.0 | 150.0 | 150.0 | 150.0 |
| Titanium Dioxide | 140.0 | 140.0 | 140.0 | 140.0 |
| EF Acrylic Latex 1 | 458.0 | 458.0 | 458.0 | 458.0 |
| Polyfunctional Amine (1-x[-b]-2') | 11.0 | | 11.0 | 0.0 |
| Polyfunctional Amine (1-x[-b]-1) | | 11.0 | | |
| Methyl Alcohol | 35.0 | 35.0 | 35.0 | 35.0 |
| Propylene Glycol | 3.0 | 3.0 | 3.0 | 3.0 |
| Water | 10.6 | 10.3 | 9.3 | 11.3 |
| Waterborne Float Solution Intermediate | 10.0 | 10.0 | 10.0 | 10.0 |
| Glycol Ether Solvent | | 10.0 | | |
| Coalescent | 20.0 | 10.0 | 20.0 | 20.0 |

Example Testing and Results

The viscosity, water resistance, scrub resistance and color changes associated with white paints formed from coating compositions containing an anionically stabilized acrylic-based copolymer and the polyfunctional amines according to structures (I-x[-b]-1), (I-x[-b]-2'), or a commercially available quick drying agent (CQDA) are provided in Tables 2-6:

Viscosity

Paint viscosity is determined by measuring Krebs Units (Ku) using a paddle type viscometer according to ASTM D562. Viscosities of 80 to 90 Ku are considered suitable for testing.

When the formulation(s) was complete, the off the mill (OTM) viscosity (KU) and pH of the paints were measured and recorded. The formulation KU and pH was retested after being allowed to sit overnight.

In a further aspect of this disclosure, the change in Krebs Units (ΔKU) should be less than or equal to 10 Ku and preferably less than 7 Ku, when measured per ASTM-562, entitled "Standard Test Method for Consistency of Paints Measuring Krebs Unit (KU) Using a Stormer-Type Viscometer". A ΔKu of greater than 10 Ku is considered a formulation failure and the coating is not viable for commercial use for traffic paint compositions.

An "off-the-mill" (OTM) sample of each paint formulation was obtained after processing through a grinding mill. The initial viscosity of the sample was recorded as OTM Ku. As viscosities suitable for testing are in the range of 80-90 Ku, a non-ionic, water soluble hydroxyethyl cellulose thickener can be added to raise the viscosity to within the suitable range for testing. An example thickener is Natrosol HBR 250. Once the formulation is thickened it is allowed to sit overnight and then the pH and the overnight Ku are measured. Adjustment of viscosity is continued until a suitable viscosity is reached or the viscosity is no longer adjustable as the viscosity has increased beyond the useable limit. The viscosity of each white acrylic latex composition containing a polyfunctional amine crosslinker as a fast drying agent is presented in Table 2.

Example 1 presented an insufficient initial viscosity measurement and was allowed to sit overnight in order to allow for complete activation of the thickener and equilibration of the formulation. The overnight Ku was measured at 80.6 with a pH of 10.34. 0.15 g thickener was added to increase the viscosity to within the measurable range of 80-90 Ku. Viscosity was measured after the addition of thickener at 82.2 Ku. The formulation was again allowed to sit overnight where the viscosity was again measured and determined to be 83.20 Ku with a pH of 10.34. After a 2 week period of heat stability, the final Ku was measured at 139.70. The change in viscosity was recorded as ΔKu=56.50. Data recorded for this formulation is not suitable for further testing.

Example 2 had an initial OTM Ku measurement of 79.1 Ku. 0.19 g thickener was added to increase the viscosity to within the measurable range of 80-90 Ku. The OTM Ku was measured after addition of the thickener as 83.60 Ku. The formula was allowed to sit overnight and the Overnight Ku was measured as 84.0 Ku. The Overnight pH was measured at 10.25. No further viscosity adjustment was needed. After a 2 week period of heat stability, the final Ku was measured at 86.70 Ku. The change in viscosity was recorded as ΔKu=2.70.

Example 3 had an initial OTM Ku measurement of 76.6 Ku. 0.29 g thickener was added to increase the viscosity to within the measurable range of 80-90 Ku. The formula was allowed to sit overnight and the Overnight Ku was measured as 84.8 Ku. The Overnight pH was measured at 10.07. No further viscosity adjustment was needed and the final Ku, after a 2 week period of heat stability, was measured at 85.6 Ku. The change in viscosity was recorded as ΔKu=0.8.

Example 4 had an initial OTM Ku measurement of 84.8 Ku. No additional thickener was added to increase the viscosity to within the measurable range of 80-90 Ku. The formula was allowed to sit overnight and the Overnight Ku was measured as 84.8 Ku. The Overnight pH was measured at 10.10. No further viscosity adjustment was needed and the final Ku, after a 2 week period of heat stability, was measured at 85.6 Ku. The change in viscosity was recorded as ΔKu=0.8.

TABLE 2

Krebs Unit Viscosity of Acrylic Latex Compositions Containing a Polyfunctional Amine Crosslinker as a Fast Drying Agent (White)

| | Example 1 | Example 2 | Example 3 | Example 4 |
|---|---|---|---|---|
| OTM Ku | | 79.1 | 76.6 | 84.8 |
| HIT HBR 250 grams | | 0.19 | 0.29 | |
| OTM Ku | | 83.60 | | |
| Overnight Ku | 80.6 | 84.0 | 84.8 | 84.8 |
| Overnight pH | 10.34 | 10.25 | 10.07 | 10.10 |
| HIT HBR 250 grams | 0.15 | | | |
| OTM Ku | 82.2 | | | |
| Overnight Ku | 83.20 | | | |
| Overnight pH | 10.34 | | | |
| Heat Stability Ku | 139.70 | 86.70 | 85.6 | 85.6 |
| ΔKu | 56.50 | 2.70 | 0.8 | 0.8 |

As shown below in Table 3, the composition containing an anionically stabilized acrylic-based copolymer and a polyfunctional amine of Structure (I-x[-b]-2'), (Example 3) exhibited a ΔKu of 0.8 with a dry time according to ASTM standard D711 of 8 minutes, and with a 75% humidity dry time of 11 minutes. The addition of I-x[-b]-2' in the latex improved the water-resistance and dry time of the coatings with compositions containing 11 lbs/100 gallons of (I-x[-b]-2') and was suitable for road pavement paint.

Having the amines produced separately from the latex formulations provides flexibility to adjust final paint formulations using selected polyfunctional amines. By varying the concentration of the polyfunctional amines, one may tailor the final paint formulations, thereby meeting additional and varied consumer specifications.

TABLE 3

Test Results for Dry times at 50% and 75% RH and final ΔKu Values as Measured Using ASTM D711 Examples 1-4 (White Paint)—Dry Time is in Minutes

| Description | Example 1 | Example 2 | Example 3 | Example 4 |
|---|---|---|---|---|
| D711 dry time | 8 | 7 | 8 | 7 |
| 75% humidity dry time | 10 | 11 | 11 | 10 |
| ΔKu | 56.50 | 2.7 | 0.8 | 0.8 |

Drawdown samples were prepared via the procedure provided herein:

A sample of paint was drawn to 15 mil wet film thickness onto to a clean black scrub test panel and allowed to dry horizontally for 30 to 60 minutes at ambient temperature and 50 to 55% relative humidity. When the drying time is complete, the samples were placed vertically into a vessel of 72° F.±2° F. still tap water and allowed to remain there for 30 minutes, during which time the film is observed for effects of water damage and times of noted damage is recorded. After completion of the test, the samples were then removed from the water and further observed noting the percentage of wash off erosion, percentage of blistering of area exposed to water during test, and size of the blisters (Small≤5 mm, Medium 5-10 mm, Large≥10 mm). Recovery of blistering is measured as Pass/Fail. Pass was determined as a complete recovery of blistering after drying of the sample. Failure was determined if the film still showed effects of blistering after complete drying of the sample.

Results of water immersion testing according to ASTM 870-09 are provided in Table 4 for white formulations, Examples 2-4. Example 1 was not a viable formulation and therefore was not suitable for further testing which is the reason that no further test results are provided. Within Table 4, only Example 2 passed the test. Example 3 and 4 exhibited delamination of the paint from the substrate.

TABLE 4

Water Immersion Performance of Compositions Containing Polyfunctional Amine Crosslinkers as a Fast Drying Agent (White)—All numbers in Table 4 correspond to minutes and seconds prior to inspection and determination

| Water Immersions | Example 1 | Example 2 | Example 3 | Example 4 |
|---|---|---|---|---|
| 30 min 1st failure | | 3:36 partial delamination | 4:48 partial delamination | 3:41 partial delamination |
| 30 min 2nd failure | | 21:15 total delamination | 11:14 total delamination | 21:24 total delamination |
| 45 min 1st failure | | 6:36 sagging blisters @ waterline | 4:48 partial delamination | 4:00 partial delamination |
| 45 min 2nd failure | | 15:08 small blisters @ waterline | 12:12 total delamination | 20:25 total delamination |
| 45 min 3rd failure | | 21:16 partial delamination | | |
| 60 min 1st failure | | 5:10 small blisters @ waterline | 7:03 small blisters @ waterline | 3:30 partial delamination |
| 60 min 2nd failure | | 10.03 small blisters throughout | 12:14 partial delamination | 21:01 total delamination |
| 60 min 3rd failure | | | | |
| 60 min 4th failure | | | | |
| 60 min Recovery | | Recovered | | |

*Water immersion data for EXAMPLE 1 was not achieved as the paint formulation did not meet the initial specification of ΔKu≤10 Ku and warranted no further investigations.

Scrub Resistance

The scrub resistance of the white formulations were tested according to ASTM D2486-00, "Standard Test Methods for Scrub Resistance of Wall Paints". The results are provided in Table 5. According to Section 10.1.2 of the standard, an improvement is identified as results presenting at >100% of the Sample % Control. For this test method, the standard used was Fastrack 2706®, an all acrylic water borne pavement marking traffic paint which has been manufactured by Dow Chemical of Midland, Mich. for more than 20 years, herein also referred to as the "Control".

The color performance data of the viable white compositions containing polyfunctional amine crosslinkers of the present disclosure were tested according to ASTM D2805-96a, "Standard Test Method for Hiding Power of Paints by Reflectometry", are provided in Table 6. The acceptable range of opacity according to the standard is between 77.16% and 99.00%. Example 1 provided no testable final formulation and therefore no results were obtained.

TABLE 6

Color Performance of Compositions Containing a Polyfunctional Amine Crosslinker as a Fast Drying Agent (White) Using ASTM D2805-96a

| Color | Example 2 | Example 3 | Example 4 |
|---|---|---|---|
| DL* | 2.04 L | 1.91 L | 2.00 L |
| Da* | 1.40 R | 1.40 R | 1.40 R |
| Db* | −4.24 B | −4.34 B | −4.31 B |
| DE* | 4.91 | 4.95 | 4.95 |
| Opacity (%) | 99.21 | 99.53 | 99.48 |

Acrylic Latex Compositions Containing a Polyfunctional Amine Crosslinker as a Fast Drying Agent (Yellow)

Yellow elastomeric coatings containing an anionically stabilized acrylic-based copolymer and a polyfunctional amine of Structure (I-x[-b]-2'), a polyfunctional amine of Structure (I-x[-b]-1), or a commercially available quick drying agent (CQDA) were prepared as described below.

Example 5

For a 100 gallon (yellow paint) coating composition, the following ingredients were mixed as follows:

To produce a yellow paint composition containing a polyfunctional amine of structure (I-x[-b]-2') a quart can containing 445.0 lb of in-house aqueous polymer emulsion, also referred to as EF Acrylic Latex 1 with an addition of 11 lb of the polyfunctional amine crosslinker (I-x[-b]-2'), and stirred for 5 minutes using a high sheer mixing blade at moderate speed. Next, 6.0 lb defoamer, 8.0 lb acrylic latex dispersant, 3 lb nonylphenol ethoxylate surfactant, and 0.13 lb thickener were added while stirring the latex/crosslinker solution with a high sheer mixing blade at a moderate speed for another 5 minutes. Next, 10.28 lb of water was added to the stirring mixture and stirred at high speed for another 5

TABLE 5

Scrub Cycle Performance of Compositions Containing a Polyfunctional Amine Crosslinker as a Fast Drying Agent (White) - All Numbers in Table 5 correspond to the number of scrub cycles performed or the TVL (threshold value) Factor

| | Scrub Cycles | | TVL Factor 1.0262 | | | | Sample % |
|---|---|---|---|---|---|---|---|
| Formula | Control | sample | Std Control | Std Sample | Sample Avg | Control avg | of Control |
| EXAMPLE 2 | 562 | 1007 | 577 | 1033 | 1106 | 593 | 186.59% |
| | 620 | 1133 | 636 | 1163 | | | |
| | 589 | 1174 | 604 | 1205 | | | |
| | 540 | 998 | 554 | 1024 | | | |
| EXAMPLE 3 | 536 | 663 | 550 | 680 | 846 | 621 | 136.22% |
| | 633 | 907 | 650 | 931 | | | |
| | 606 | 928 | 622 | 952 | | | |
| | 646 | 800 | 663 | 821 | | | |
| EXAMPLE 4 | 481 | 846 | 494 | 868 | 986 | 569 | 173.51% |
| | 591 | 938 | 606 | 963 | | | |
| | 580 | 1081 | 595 | 1109 | | | |
| | 564 | 980 | 579 | 1006 | | | |
| Avg of Control | 579 | | | | | | |
| St. Dev | 46 | | | | | | | minutes. To this, approximately 12 lb ammonia was added to obtain a solution of pH 10. Then pigments and fillers including 23 lb Titanium dioxide, 560.0 lb Calcium carbonate, 24.6 lb organic yellow pigment, 1.5 lb yellow iron oxide, and 170 lb. silica were added carefully while stirring at high speed for 15 minutes. After completion of the mixing and accompanying grinding, 35 lb of a solvent (such as methyl alcohol) was added slowly and at reduced stirring speed while adding 3.0 lb propylene glycol and 10 lb of a waterborne float solution intermediate. Then 23.0 lb of the coalescent was added to the mixture. The final mixture was allowed to stir continuously.

Example 6

To produce a yellow paint composition containing a commercially available quick drying agent (CQDA) a quart can containing 445.0 lb of in-house aqueous polymer emulsion, also referred to as EF Acrylic Latex 1 with an addition of 11 lb of the CDQA and stirred for 5 minutes using a high sheer mixing blade at moderate speed. Next, 6.0 lb defoamer, 6 lb. polycarboxylic acid dispersant, 0.13 lb thickener, 5 lb grind aid surfactant, and 4 lb. amine alkoxylated stabilizing surfactant dispersion were added while stirring the Latex/CDQA mixture with a high sheer mixing blade at a moderate speed for another 5 minutes. Next, 11.32 lb of water was added to the stirring mixture and stirred at high speed for another 5 minutes. To this, no ammonia was added to obtain a solution of pH 10. Then pigments and fillers including 23 lb Titanium dioxide, 560.0 lb., Calcium carbonate, 24.6 lb organic yellow pigment, 1.5 lb yellow iron oxide, and 170 lb silica were added carefully while stirring at high speed for 15 minutes. After completion of the mixing and accompanying grinding, 35 lb of solvent (such as methyl alcohol) and 11 lb. of butyl carbitol were added slowly and at reduced stirring speed. During this reduced stirring speed mixing, 3.0 lb propylene glycol and 10 lb of a waterborne float solution intermediate were added. Then 11.0 lb. of a coalescent solvent such as 2,2,4-Trimethyl-1,3-pentanediol monoisobutyrate was added to the mixture, which was allowed to continue stirring.

To this, no ammonia was added or required for obtaining a solution of pH 10. Then pigments and fillers including 23 lb Titanium dioxide, 560.0 lb Calcium carbonate, 24.6 lb organic yellow pigment, 1.5 lb yellow iron oxide, and 170 lb silica were added carefully while stirring at high speed for 15 minutes. After completion of the mixing and accompanying grinding, 35 lb of solvent (such as methyl alcohol) and 11 lb. of butyl carbitol were added slowly and at reduced stirring speed. During this reduced stirring speed mixing, 3.0 lb propylene glycol and 10 lb of a waterborne float solution intermediate were added Then 11.0 lb. of a coalescent solvent such as 2,2,4-Trimethyl-1,3-pentanediol monoisobutyrate was added to the mixture, which was allowed to continue stirring.

Example 7

For a 100 gallon coating composition, the following ingredients were mixed:

For a yellow paint composition containing a polyfunctional amine of Structure (I-x[-b]-1), (Example 7), to a quart can containing 445.0 lb of in-house aqueous polymer emulsion, also referred to as EF Acrylic Latex 1, was added 11 lb of polyfunctional amine crosslinker solution of structure (I-x[-b]-1), and stirred for 5 minutes using a high sheer mixing blade at moderate speed. 6.0 lb defoamer was added, 6 lb. polycarboxylic acid dispersant, 0.13 lb thickener, 5 lb grind aid surfactant, and 4 lb. amine alkoxylated stabilizing surfactant dispersion while stirring with a high sheer mixing blade at a moderate speed for another 5 minutes. Next, 9.79 lb of water was added to the stirring mixture and stirred at high speed for another 5 minutes.

To this, no ammonia was added to obtain a solution of pH 10. Then pigments and fillers including 23 lb Titanium dioxide, 560.0 lb Calcium carbonate, 24.6 lb organic yellow pigment, 1.5 lb yellow iron oxide, and 170 lb silica were added carefully while stirring at high speed for 15 minutes. After completion of the mixing and accompanying grinding, 35 lb of solvent (such as methyl alcohol) and 11 lb. of butyl carbitol were added slowly and at reduced stirring speed. During this reduced stirring speed mixing, 3.0 lb propylene glycol and 10 lb of a waterborne float solution intermediate were added. Then 11.0 lb. of a coalescent solvent such as 2,2,4-20 Trimethyl-1,3-pentanediol monoisobutyrate was added to the mixture, which was allowed to continue stirring.

Example 8

For a 100 gallon coating composition, the following ingredients were mixed:

For a yellow paint composition containing a polyfunctional amine of Structure (I-x[-b]-2'), (Example 8), to a vessel containing 445.0 lb of in-house aqueous polymer emulsion, also referred to as EF Acrylic Latex 1, was added 11 lb of polyfunctional amine crosslinker solution of structure (I-x[-b]-2'), and stirred for 5 minutes using a high sheer mixing blade at moderate speed. 6.0 lb defoamer was added, 6 lb. Polycarboxylic acid dispersant, 0.13 lb thickener, 5 lb grind aid surfactant, and 4 lb amine alkoxylated stabilizing surfactant dispersion while stirring with a high sheer mixing blade at a moderate speed for another 5 minutes. Next, 9.79 lb of water was added to the stirring mixture and stirred at high speed for another 5 minutes. To this, approximately 3.5 lb ammonia was added to obtain a solution of pH 10. Then pigments and fillers including 23 lb Titanium dioxide, 560.0 lb Calcium carbonate, 24.6 lb organic yellow pigment, 1.5 lb yellow iron oxide, and 170 lb silica were added carefully while stirring at high speed for 15 minutes. After completion of the mixing and accompanying grinding, 35 lb of a solvent (such as methyl alcohol) and 11 lb of butyl carbitol were added slowly and at reduced stirring speed. During this reduced stirring speed mixing, 3.0 lb propylene glycol and 10 lb of a waterborne float solution intermediate were added. Then 11.0 lb of a coalescent solvent such as 2,2,4-Trimethyl-1,3-pentanediol monoisobutyrate was added to the mixture, which was allowed to continue stirring.

Formulations for yellow pigmented paint, Examples 5-8 are summarized in Table 7 below:

TABLE 7

Compositions Containing a Polyfunctional Amine Crosslinker as a Fast Drying Agent (Yellow)—All numbers correspond to weight in pounds of each additive

| Description | Example 5 | Example 6 | Example 7 | Example 8 |
|---|---|---|---|---|
| Acrylic Latex Dispersant | 8.00 | | | |
| Polycarboxylic Acid Dispersant | | 6.00 | 6.00 | 6.00 |
| Nonylphenol Ethoxylate | 3.00 | | | |
| Thickener | 0.13 | 0.13 | 0.13 | 0.13 |
| Defoamer | 6.00 | 6.00 | 6.00 | 6.00 |

TABLE 7-continued

Compositions Containing a Polyfunctional Amine Crosslinker as a Fast Drying Agent (Yellow)—All numbers correspond to weight in pounds of each additive

| Description | Example 5 | Example 6 | Example 7 | Example 8 |
|---|---|---|---|---|
| Grind Aid Surfactant | | 5.00 | 5.00 | 5.00 |
| Amine alkoxylate Stabilizing Surfactant Dispersion | | 4.00 | 4.00 | 4.00 |
| CQDA | 0.00 | 11.00 | 0.00 | 0.00 |
| Calcium Carbonate | 560.00 | 560.00 | 560.00 | 560.00 |
| Silica | 170.00 | 170.00 | 170.00 | 170.00 |
| Titanium Dioxide | 23.00 | 23.00 | 23.00 | 23.00 |
| Pigment | 24.60 | 24.60 | 24.60 | 24.60 |
| Yellow Iron Oxide | 1.50 | 1.50 | 1.50 | 1.50 |
| EF Acrylic Latex 1 | 445.00 | 445.00 | 445.00 | 445.00 |
| Polyfunctional Amine (I-x[-b]-2') | 11.00 | 0.00 | | 11.00 |
| Polyfunctional Amine (I-x[-b]-1) | 0.00 | | 11.00 | |
| Butyl Capitol Solvent | | 11.00 | 11.00 | |
| Methyl Alcohol | 35.00 | 35.00 | 35.00 | 35.00 |
| Propylene Glycol | 3.00 | 3.00 | 3.00 | 3.00 |
| Water | 10.28 | 11.32 | 9.79 | 9.25 |
| Waterborne Float Solution Intermediate | 10.00 | 10.00 | 10.00 | 10.00 |
| Coalescent | 23.00 | 11.00 | 11.00 | 22.00 |

Example Testing and Results

The viscosity, water immersion, scrub resistance, and change in color data of yellow coatings formed from coating compositions containing an anionically stabilized acrylic-based copolymer and a polyfunctional amine of Structure (I-x[-b]-2'), a polyfunctional amine of Structure (I-x[-b]-1), or a commercially available quick drying agent (CQDA) were measured as described above and are shown in Tables 8-12.

An "off-the-mill" (OTM) sample of each paint formulation was obtained after processing through the grinding mill. The initial viscosity of the sample was recorded as OTM Ku. As viscosities suitable for testing are 80-90 Ku, a non-ionic, water soluble hydroxyethyl cellulose thickener can be added to raise the viscosity to within the suitable range for testing. An example thickener is Natrosol HBR 250. Once the formulation is thickened it is allowed to sit overnight and then the pH and the Overnight Ku are measured. Adjustment of viscosity is continued until a suitable viscosity for testing is reached or the viscosity exceeds an allowable use value.

Example 5 had an initial OTM Ku measurement of 70.5 Ku. 0.50 g thickener was added to increase the viscosity to within the measurable range of 80-90 Ku. The Overnight Ku was measured at 83.5 Ku, and the Overnight pH was measured at 10.18. No further viscosity adjustment was needed. After a 2 week period of heat stability, the final Ku was measured at 90.4 Ku. The change in viscosity was recorded as ΔKu=6.90.

Example 6 had an initial OTM Ku measurement of 76.0 Ku. 0.30 g thickener was added to increase the viscosity to within the measurable range of 80-90 Ku. The OTM Ku was measured after addition of the thickener as 84.30 Ku. The OTM Ku was again measured, at 84.3 Ku, and the overnight pH was measured at 9.73. No further viscosity adjustment was needed and after a 2 week period of heat stability, the final Ku was measured at 86.70 Ku. The change in viscosity was recorded as ΔKu=-2.30.

Example 7 had an Overnight Ku measurement of 70.5 Ku. The Overnight pH was measured at 9.63. 0.50 g thickener was added to increase the viscosity to within the measurable range of 80-90 Ku. The OTM Ku was measured again as 83.5 Ku. No further viscosity adjustment was needed and after a 2 week period of heat stability, the final Ku was measured at 81.3 Ku. The change in viscosity was recorded as ΔKu=-2.20.

Example 8 had an initial OTM Ku measurement of 71.6 Ku. The Overnight pH was measured at 10.04. 0.46 g thickener was added to increase the viscosity to within the measurable range of 80-90 Ku. The OTM Ku was measured again as 83.5 Ku. No further viscosity adjustment was needed. After a 2 week period of heat stability, the final Ku was measured at 81.7 Ku. The change in viscosity was recorded as ΔKu=-1.80.

TABLE 8

Viscosity of Acrylic Latex Compositions Containing a Polyfunctional Amine Crosslinker as a Fast Drying Agent (Yellow)

| | EXAMPLE 5 | EXAMPLE 6 | EXAMPLE 7 | EXAMPLE 8 |
|---|---|---|---|---|
| OTM Ku | 70.5 | 76.0 | | |
| HIT HBR 250 grams | 0.50 | 0.30 | | |
| OTM Ku | | 84.3 | | |
| Overnight Ku | 83.5 | | 70.5 | 71.6 |
| Overnight pH | 10.18 | 9.73 | 9.63 | 10.04 |
| HIT HBR 250 grams | | | 0.50 | 0.46 |
| OTM Ku | | | 83.5 | 83.5 |
| Overnight Ku | | | | |
| Overnight pH | | | | |
| Heat Stability | | | | |
| KU | 88.3 | 82.5 | 82.3 | 82.0 |
| ΔKU | 88.3 | 82.2 | 81.8 | 81.5 |
| Ku | 90.4 | 82.0 | 81.3 | 81.7 |
| ΔKU | 6.90 | -2.30 | -2.20 | -1.80 |
| pH | 9.95 | 9.60 | 9.56 | 9.92 |

As shown in Table 9, the composition containing an anionically stabilized acrylic-based copolymer and a polyfunctional amine of Structure (I-x[-b]-2'), (Example 8) exhibited ΔKu of -1.8 with a dry time according to ASTM standard D711 of 5 minutes, with a 75% humidity dry time of 12 minutes.

Table 9 below summarizes the dry time test results for Examples 5-8 for yellow paint.

TABLE 9

Test Results for Dry Times at 50 and 75% RH and Final ΔKu Values as Measured Using ASTM D711 Examples 5-8 (Yellow Paint)—All dry times listed are in minutes

| Description | Example 5 | Example 6 | Example 7 | Example 8 |
|---|---|---|---|---|
| D711 dry time | 5 | 7 | 6 | 7 |
| 75% humidity dry time | 10 | 11 | 11 | 12 |
| ΔKU | 6.90 | -2.30 | -2.20 | -1.80 |

The scrub resistance of the yellow formulations were tested according to ASTM D2486-00, "Standard Test Methods for Scrub Resistance of Wall Paints". The results are provided in Table 10. According to Section 10.1.2 of the standard, an improvement is identified as results presenting at >100% of the Sample % Control. For this test method, the standard used was Fastrack 2706®, an all acrylic water borne pavement marking traffic paint which has been manufactured by Dow Chemical of Midland, Mich. for more than 20 years, herein also referred to as the "Control".

TABLE 10

Scrub Cycle Performance of Compositions Containing a Polyfunctional Amine Crosslinker as a Fast Drying Agent (Yellow) - All Numbers in Table 5 correspond to the number of scrub cycles performed or the TVL (threshold value) Factor

| Formula | Scrub Cycles Control | sample | TVL Factor 1.0262 Std Control | Std Sample | Sample Avg | Control avg | Sample % of Control |
|---|---|---|---|---|---|---|---|
| EXAMPLE 5 | 423 | 612 | 434 | 628 | 671 | 496 | 135.23% |
|  | 459 | 618 | 471 | 634 |  |  |  |
|  | 550 | 739 | 564 | 758 |  |  |  |
|  | 501 | 645 | 514 | 662 |  |  |  |
| EXAMPLE 6 | 452 | 792 | 464 | 813 | 937 | 521 | 179.90% |
|  | 511 | 885 | 524 | 908 |  |  |  |
|  | 524 | 1000 | 538 | 1026 |  |  |  |
|  | 543 | 975 | 557 | 1001 |  |  |  |
| EXAMPLE 7 | 489 | 889 | 502 | 912 | 952 | 523 | 181.99% |
|  | 531 | 945 | 545 | 970 |  |  |  |
|  | 544 | 968 | 558 | 993 |  |  |  |
|  | 474 | 907 | 486 | 931 |  |  |  |
| EXAMPLE 8 | 510 | 706 | 523 | 724 | 815 | 629 | 129.67% |
|  | 665 | 825 | 682 | 847 |  |  |  |
|  | 675 | 852 | 693 | 874 |  |  |  |
|  | 600 | 794 | 616 | 815 |  |  |  |
| Avg of Control | 528 |  |  |  |  |  |  |
| St. Dev | 70 |  |  |  |  |  |  |

The color performance data of the viable yellow compositions containing a polyfunctional amine crosslinker of the disclosure according to ASTM D2805-96a, "Standard Test Method for Hiding Power of Paints by Reflectometry", are provided in Table 11. The acceptable range of opacity according to the standard is 77.16% to 99.00%.

TABLE 11

Opacity of Compositions Containing a Polyfunctional Amine Crosslinker as a Fast Drying Agent (Yellow) Using ASTM D2805-96a

| Color | Example 5 | Example 6 | Example 7 | Example 8 |
|---|---|---|---|---|
| DL* | 4.84 L | 4.68 L | 4.59 L | 4.71 L |
| Da* | −1.58 G | −1.26 G | −1.32 G | 1.40 G |
| Db* | 1.79 Y | 1.26 Y | 1.70 Y | 1.68 Y |
| DE* | 5.40 | 5.01 | 5.07 | 5.19 |
| Opacity (%) | 96.68 | 97.69 | 97.23 | 96.37 |

The compositions and methods of the appended claims are not limited in scope by the specific compositions and methods described herein, which are intended as illustrations of a few aspects of the claims and any compositions and methods that are functionally equivalent are intended to fall within the scope of the claims.

Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein as well as combinations of steps, elements, components, and constituents are included though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of and "consisting of can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, and not to be construed in light of the number of significant digits and ordinary rounding approaches.

What is claimed is:

1. An aqueous latex paint comprising:
    (a) one or more anionically stabilized acrylic copolymers;
    (b) one or more polyfunctional amines of a structure as provided by I-x-b-1 and/or I-x-b-2';

(I-x-b-1)

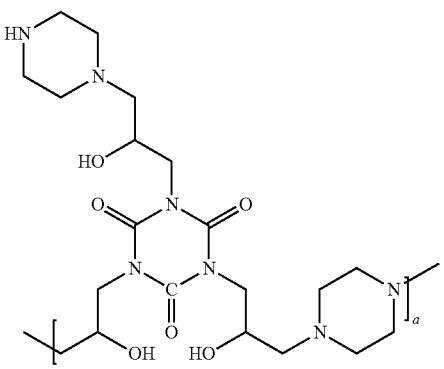

-continued

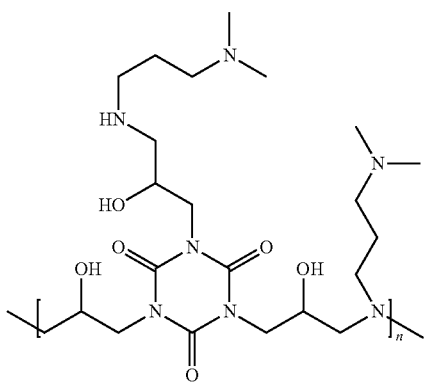

(I-x-b-2');

and (c) at least one volatile base, wherein said polyfunctional amines further comprises one or more variations of structures I-x-b-1 and I-x-b-2' provided as I-x-b-1' and I-x-b-2" so that a final polyfunctional amine structure is partially or fully saturated and/or highly branched, wherein:

(I-x-b-1') is represented as:

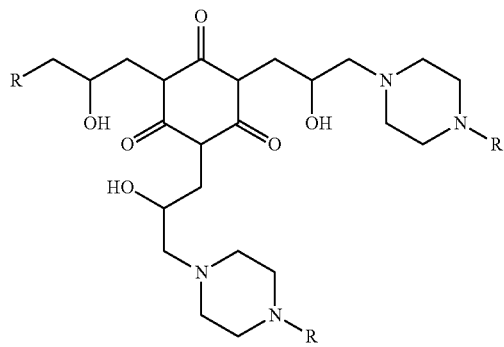

wherein R=H or a next repeating unit, wherein said next repeating unit is represented as (I-x-b-1'-RU):

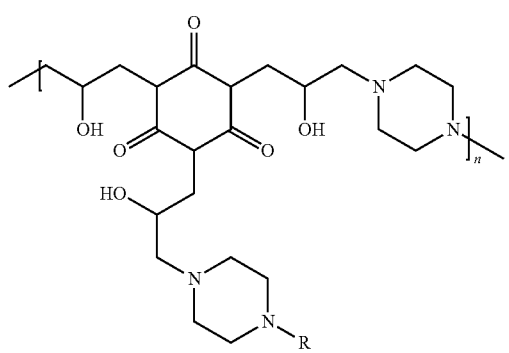

-continued

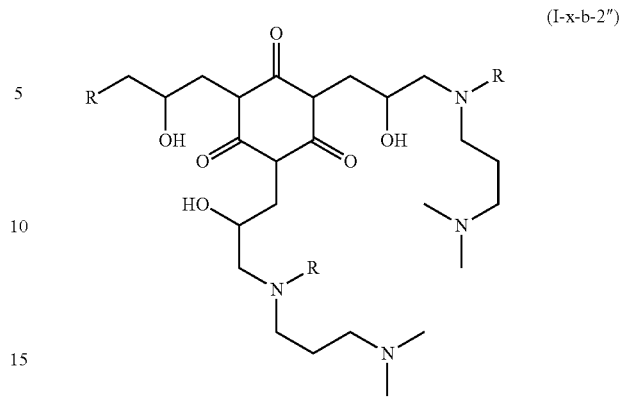

(I-x-b-2")

wherein R=H or said next repeating unit, wherein said next repeating unit is represented as (I-x-b-2"-RU),

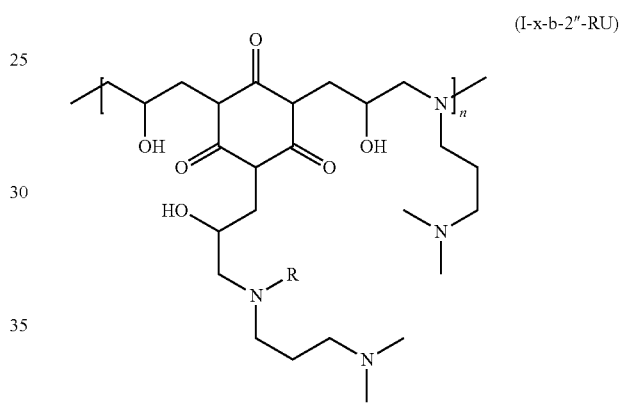

(I-x-b-2"-RU)

wherein n is a number between 1 and 100,
and wherein $M_n$ is 5,000 to 20,000 Daltons.

2. The paint of claim 1, wherein said paint provides for dry times on paved surfaces in an atmosphere that is characterized as possessing at least 50% relative humidity with a final ΔKu value of no greater than 10.0, as measured using ASTM D711.

3. The paint of claim 1, wherein said paint provides for dry times on paved surfaces, in an atmosphere that is characterized as possessing at least 75% relative humidity, with a final ΔKu value of no greater than 10.0, as measured using ASTM D711.

4. The paint of claim 1, wherein said paint provides for water resistance that reduces or eliminates blistering, wherein said paint is tested according to ASTM D870 for water immersion.

5. The paint of claim 1, wherein said paint provides for water resistance that improves scrub resistance as compared to said paint with commercially available quick drying agents (CQDA's) by at least 30% wherein said paint is tested according to ASTM D 2486 for water immersion.

6. The paint of claim 1, wherein said paint provides for water resistance that improves color fastness by improving opacity to at least 98% as compared to said paint with commercially available quick drying agents (CQDA's) wherein said paint is tested according to ASTM D 2850 for color opacity.

7. The paint of claim 1, wherein said paint further comprises white pigment.

8. The paint of claim 1, wherein said paint further comprises yellow pigment.

9. The paint of claim 1, wherein said polyfunctional amine has an average molecular weight of between 100 and 500,000 Daltons.

10. The paint of claim 1, wherein said polyfunctional amine has an average molecular weight of between 5,000 and 20,000 Daltons.

11. The paint of claim 1, wherein said polyfunctional amine is present in said paint at between 0.1% by weight and 5% by weight, based on a dry weight of the anionically stabilized copolymer.

12. The paint of claim 1, wherein said polyfunctional amine is present in said paint at between 0.5% by weight and 2.5% by weight, based on a dry weight of the anionically stabilized copolymer.

13. The paint of claim 1, wherein said paint further comprises one or more additional polymers.

14. The paint of claim 1, wherein said paint further comprises at least one of: pigments, fillers, dispersants, coalescents, pH modifying agents, plasticizers, defoamers, surfactants, thickeners, biocides, or co-solvents.

15. The paint of claim 1, wherein said paint further comprises at least one of: rheology modifiers, wetting and spreading agents, leveling agents, conductivity additives, adhesion promoters, anti-blocking agents, anti-cratering agents and anti-crawling agents, anti-freezing agents, corrosion inhibitors, anti-static agents, flame retardants and intumescent additives, dyes, optical brighteners and fluorescent additives, UV absorbers and light stabilizers, chelating agents, cleanability additives, crosslinking agents, flatting agents, flocculants, humectants, insecticides, lubricants, odorants, oils, waxes and slip aids, soil repellants, or stain resisting agents.

16. The paint of claim 1, wherein said paint includes aqueous dispersions having a solids content of between 45% and 65% by weight of a total paint formulation.

17. The paint of claim 1, wherein said paint includes aqueous dispersions having a solids content of between 60% and 77% by weight of a total paint formulation.

18. The paint of claim 1, wherein said paint is applied to a surface selected from the group consisting of metal, asphalt, concrete, stone, ceramic, wood, plastic, polyurethane foam, glass, and combinations thereof.

19. The paint of claim 1, wherein said paint exists as a coating that has a dry thickness of between 10 mils and 100 mils.

* * * * *